United States Patent
Yasukawa et al.

(10) Patent No.: US 11,738,068 B2
(45) Date of Patent: Aug. 29, 2023

(54) PROTEIN-CONTAINING AQUEOUS LIQUID FORMULATION

(71) Applicant: JCR Pharmaceuticals Co., Ltd., Ashiya (JP)

(72) Inventors: Hidehito Yasukawa, Kobe (JP); Takashi Hanada, Kobe (JP); Junya Tani, Kobe (JP); Shinji Okabe, Kobe (JP); Yuuka Asano, Kobe (JP)

(73) Assignee: JCR Pharmaceuticals Co., Ltd., Ashiya (JP)

( * ) Notice: Subject to any disclaimer, the term of this patent is extended or adjusted under 35 U.S.C. 154(b) by 71 days.

(21) Appl. No.: 17/253,458

(22) PCT Filed: Jun. 25, 2019

(86) PCT No.: PCT/JP2019/025096
§ 371 (c)(1),
(2) Date: Dec. 17, 2020

(87) PCT Pub. No.: WO2020/004368
PCT Pub. Date: Jan. 2, 2020

(65) Prior Publication Data
US 2021/0252112 A1    Aug. 19, 2021

(30) Foreign Application Priority Data
Jun. 25, 2018   (JP) .................... 2018-119494

(51) Int. Cl.
| | | |
|---|---|---|
| A61K 38/02 | (2006.01) |
| A61K 38/27 | (2006.01) |
| A61K 38/43 | (2006.01) |
| A61K 39/395 | (2006.01) |
| A61K 47/04 | (2006.01) |
| A61K 9/08 | (2006.01) |
| A61K 45/06 | (2006.01) |
| A61K 47/10 | (2017.01) |
| A61K 47/26 | (2006.01) |
| C07K 16/28 | (2006.01) |

(52) U.S. Cl.
CPC ............. *A61K 38/27* (2013.01); *A61K 38/43* (2013.01); *A61K 45/06* (2013.01); *A61K 47/10* (2013.01); *A61K 47/26* (2013.01); *C07K 16/2818* (2013.01); *C07K 16/2827* (2013.01)

(58) Field of Classification Search
CPC combination set(s) only.
See application file for complete search history.

(56) References Cited

U.S. PATENT DOCUMENTS

| | | |
|---|---|---|
| 5,096,885 A | 3/1992 | Pearlman et al. |
| 5,126,324 A | 6/1992 | Clark et al. |
| 5,597,797 A | 1/1997 | Clark |
| 5,783,559 A | 7/1998 | Florin-Robertsson et al. |
| 2004/0170632 A1 | 9/2004 | Mahler et al. |
| 2005/0053598 A1 | 3/2005 | Burke et al. |
| 2006/0029635 A1 | 2/2006 | Siebold et al. |
| 2006/0165733 A1 | 7/2006 | Betz et al. |
| 2007/0014818 A1 | 1/2007 | Betz |
| 2007/0065469 A1 | 3/2007 | Betz et al. |
| 2010/0021461 A1 | 1/2010 | Burke et al. |
| 2011/0201554 A1 | 8/2011 | Choi et al. |
| 2011/0318323 A1 | 12/2011 | Zhu et al. |
| 2011/0318324 A1 | 12/2011 | Salamat-Miller et al. |
| 2011/0318327 A1 | 12/2011 | Concino et al. |
| 2012/0003202 A1 | 1/2012 | Calias et al. |
| 2012/0009171 A1 | 1/2012 | Salamat-Miller et al. |
| 2012/0014936 A1 | 1/2012 | Natoli et al. |
| 2012/0232021 A1 | 9/2012 | Martini et al. |
| 2012/0328614 A1 | 12/2012 | Burke et al. |
| 2013/0071386 A1 | 3/2013 | Burke et al. |
| 2013/0295071 A1 | 11/2013 | Salamat-Miller et al. |
| 2013/0295077 A1 | 11/2013 | Concino et al. |
| 2014/0187502 A1 | 7/2014 | Martini et al. |
| 2014/0194356 A1 | 7/2014 | Pragl et al. |
| 2014/0271598 A1 | 9/2014 | Zhu et al. |
| 2015/0044206 A1 | 2/2015 | Burke et al. |
| 2016/0152959 A1 | 6/2016 | Martini et al. |
| 2016/0158324 A1 | 6/2016 | Zhu et al. |
| 2016/0243242 A1 | 8/2016 | Choi et al. |

(Continued)

FOREIGN PATENT DOCUMENTS

| | | |
|---|---|---|
| CN | 102368070 A | 3/2012 |
| JP | H08-505617 | 6/1996 |

(Continued)

OTHER PUBLICATIONS

International Search Report dated Sep. 10, 2019 in PCT/JP2019/025096 filed on Jun. 25, 2019, 3 pages.
Extended European Search Report dated Feb. 10, 2022 in Extended European Patent Application No. 19827465.6, 14 pages.
Medical package insert of Growject S.C. 6mg with unedited computer-generated English transration, 19 total pages.
International Search Report dated Sep. 10, 2019 in PCT/JP2019/025096 filed Jun. 25, 2019, 3 pages.

(Continued)

*Primary Examiner* — Julie Ha
*Assistant Examiner* — Kristina M Hellman
(74) *Attorney, Agent, or Firm* — Oblon, McClelland, Maier & Neustadt, L.L.P.

(57) ABSTRACT

An aqueous preparation containing a protein as an active ingredient which is stable in storage in solution and makes an injection pain reduced is provided. More specifically an aqueous preparation containing a phosphate buffer at a concentration of 1 to 20 mM and a protein as an active ingredient is provided. Further more specifically provided is an aqueous preparation containing a phosphate buffer at a concentration of 1 to 20 mM, human growth hormone as an active ingredient, a poloxamer as a non-ionic surfactant; and phenol as a isotonic agent.

4 Claims, 1 Drawing Sheet

(56) References Cited

U.S. PATENT DOCUMENTS

| | | |
|---|---|---|
| 2016/0369001 A1 | 12/2016 | Sonoda et al. |
| 2017/0042977 A1 | 2/2017 | Natoli et al. |
| 2017/0042978 A1 | 2/2017 | Calias et al. |
| 2018/0071212 A1 | 3/2018 | Salamat-Miller et al. |
| 2018/0085438 A1 | 3/2018 | Concino et al. |
| 2018/0194843 A1 | 7/2018 | Burke et al. |
| 2018/0244754 A1 | 8/2018 | Takahashi et al. |
| 2018/0256722 A1 | 9/2018 | Pragl et al. |
| 2019/0183984 A1 | 6/2019 | Natoli et al. |
| 2020/0247872 A1 | 8/2020 | Takahashi et al. |
| 2020/0297821 A1 | 9/2020 | Moshashaee et al. |
| 2021/0269507 A1 | 9/2021 | Takahashi et al. |

FOREIGN PATENT DOCUMENTS

| | | |
|---|---|---|
| JP | 2003-504346 A5 | 2/2003 |
| JP | 2004-536129 A | 12/2004 |
| JP | 2005-535651 A | 11/2005 |
| JP | 2013-538788 A | 10/2013 |
| JP | 2014-28831 A | 2/2014 |
| JP | 2014-528919 A | 10/2014 |
| PA | 2003-504346 A | 2/2003 |
| WO | WO 94/15584 A1 | 7/1994 |
| WO | WO 97/07816 A1 | 3/1997 |
| WO | WO 01/03741 A1 | 1/2001 |
| WO | WO 03/007988 A1 | 1/2003 |
| WO | WO 2011/099036 A2 | 8/2011 |
| WO | WO 2012/144579 A1 | 10/2012 |
| WO | WO 2015/098989 A1 | 7/2015 |
| WO | WO 2017/043569 A1 | 3/2017 |
| WO | WO 2017/147414 A1 | 8/2017 |
| WO | WO 2018/124277 A1 | 7/2018 |
| WO | WO 2019/049967 A1 | 3/2019 |

OTHER PUBLICATIONS

Roberts J., "Protein Aggregation and Its Impact on Product Quality", Curr Opin Biotechnol. (2014), pp. 211-217.

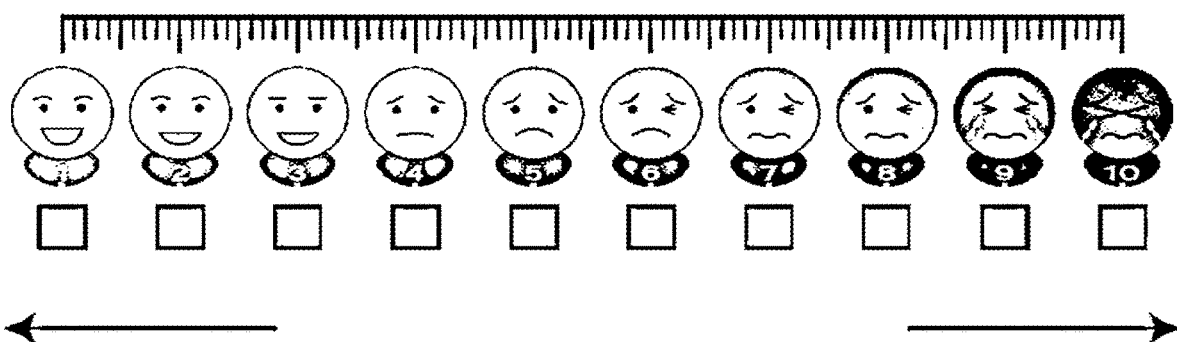

PROTEIN-CONTAINING AQUEOUS LIQUID FORMULATION

CROSS-REFERENCE TO RELATED APPLICATIONS

The present application is a U.S. national stage of International Application No. PCT/JP2019/025096, filed Jun. 25, 2019, which is based upon and claims the benefits of priority to Japanese Application No. 2018-119494, filed Jun. 25, 2018. The entire contents of all of the above applications are incorporated herein by reference.

TECHNICAL FIELD

The present invention relates to an aqueous preparation containing a protein as an active ingredient which is stable in storage in solution and makes the injection pain reduced, and specifically, relates to an aqueous preparation which contains a protein as an active ingredient and as a phosphate buffer at a concentration of 1 to 20 mM as a buffer.

BACKGROUND OF THE INVENTION

Various pharmaceutical preparations containing an active ingredient a protein have been developed. Most of these proteins are a recombinant protein prepared by using a gene recombination technology. A pharmaceutically prepared protein, having a high molecular weight, is not absorbed by oral administration, thus it is exclusively administered by subcutaneous injection, intramuscular injection, intravenous injection, or the like. Accordingly, the administration is accompanied by a pain because an injection needle is inserted. The ingredient contained in the pharmaceutical preparation affects the degree of pain.

Wild type growth hormone (hGH) is a single-chain polypeptide hormone containing 191 amino-acid residues. The hGH has been used as a therapeutic agent for growth hormone deficiency dwarfism, dwarfism in a Turner's syndrome, adult growth hormone deficiency, or the like.

In a therapy using the hGH, the hGH should be intramuscularly injected 2 to 4 times a week subcutaneously or 6 to 7 times a week intramuscularly for a long term, generally for one or more years. Accordingly, in order to reduce a burden of a patient by an ambulant treatment, self-injection at home is generally performed in the therapy using the hGH. In addition, an hGH preparation is conventionally a freeze-dried preparation, but as the freeze-dried preparation has to be dissolved with a solvent when it is used. Thus, in order to improve the convenience of the patient, an aqueous preparation in which the hGH is dissolved in advance has been developed (Non-Patent Document 1).

The hGH is intramuscularly or subcutaneously injected to the patient, and a therapy target of the hGH is generally a child. Accordingly, it has been more strongly desired that the injection of the hGH preparation is accompanied by a less pain.

PRIOR ART DOCUMENT

Non-Patent Documents

[Non-Patent Document 1] Growject S.C. Injection 6 mg/Growject S.C. Injection 12 mg Appended Paper (2017)

SUMMARY OF THE INVENTION

Technical Problem

The objective of the present invention is to provide an aqueous preparation containing a protein as an active ingredient which is stable in storage in solution and makes the injection pain reduced, specifically, to provide an aqueous preparation which contains a protein as an active ingredient In the studies for the above-mentioned object, the inventors have found that an injection pain can be reduced while stability in an aqueous preparation of a growth hormone is maintained, by setting a buffer contained in an aqueous preparation to a phosphate buffer having a concentration of 1 to 20 mM, and thus, have completed the invention. Thus the present invention includes what follows:

1. An aqueous preparation comprising phosphate buffer at a concentration of 1 to 20 mM and a protein as an active ingredient.
2. The aqueous preparation according to 1 above, wherein the concentration of the phosphate buffer is 5 to 16 mM.
3. The aqueous preparation according to 2 above, wherein the concentration of the phosphate buffer is 8 to 12 mM.
4. The aqueous preparation according to any one of 1 to 3 above, wherein the concentration of the protein is 1 to 50 mg/mL.
5. The aqueous preparation according to any one of 1 to 4 above, further containing a non-ionic surfactant.
6. The aqueous preparation according to 5 above, wherein the non-ionic surfactant is polysorbate or poloxamer.
7. The aqueous preparation according to 5 above, wherein the non-ionic surfactant is selected from the group consisting of polysorbate 20, polysorbate 80, and poloxamer 188.
8. The aqueous preparation according to any one of 5 to 7 above, wherein the concentration of the non-ionic surfactant is 1 to 10 mg/mL.
9. The aqueous preparation according to any one of 1 to 8 above, further containing an antiseptic agent.
10. The aqueous preparation according to 9 above, wherein the antiseptic agent is benzyl alcohol or phenol.
11. The aqueous preparation according to 9 above, wherein the antiseptic agent is benzyl alcohol, and the concentration of the benzyl alcohol is 2 to 20 mg/mL.
12. The aqueous preparation according to 9 above, wherein the antiseptic agent is phenol, and the concentration of the phenol is 1 to 10 mg/mL.
13. The aqueous preparation according to any one of 1 to 12 above, further containing an isotonic agent.
14. The aqueous preparation according to 13 above, wherein the isotonic agent is a neutral salt or sugar alcohol.
15. The aqueous preparation according to 13 above, wherein the isotonic agent is sodium chloride or D-mannitol.
16. The aqueous preparation according to any one of 1 to 15 above, wherein pH is 5.5 to 7.2.
17. The aqueous preparation according to 1 above, wherein the aqueous preparation contains 1 to 50 mg/mL of the protein, 5 to 16 mM of the phosphate buffer, 1.8 to 2.2 mg/mL of poloxamer 188, 2.8 to 3.8 mg/mL of phenol, and 35 to 45 mg/mL of D-mannitol, and the pH is 6.0 to 6.4.
18. The aqueous preparation according to any one of 1 to 17 above, wherein the protein is selected from the group consisting of a growth hormone, somatomedin, insulin, glucagon, a lysosome enzyme, a cytokine, a lymphokine, a blood clotting factor, an antibody, a fusion protein of an antibody and another protein, granulocyte-macrophage colony-stimulating factor (GM-CSF), granulocyte colony-stimulating factor (G-CSF), macrophage colony-stimulating factor (M-CSF), erythropoietin, darbepoetin, tissue plasminogen activator (t-PA), thrombomodulin, follicle-stimulating hormone (FSH), gonadotropic hormone-releasing hormone (GnRH), gonadotropin, DNaseT, thyroid-stimulating hormone (TSH), nerve growth factor (NGF), ciliary neurotrophic factor (CNTF), glial cell line-derived neurotrophic factor (GDNF), neurotrophin 3, neurotrophin 4/5, neurotrophin 6, neuregulin 1, activin, basic fibroblast growth factor (bFGF), fibroblast growth factor 2 (FGF2), epithelial cell growth factor (EGF), vascular endothelial growth factor (VEGF), interferon α, interferon β, interferon γ, interleukin 6, PD-1, a PD-1 ligand, tumor necrosis factor α receptor (TNF-α receptor), an enzyme having activity for decomposing beta-amyloid, etanercept, pegvisomant, metreleptin, abatacept, asfotase, and a GLP-1 receptor agonist.

19. The aqueous preparation according to any one of 1 to 17 above, wherein the protein is selected from the group consisting of a mouse antibody, a humanized antibody, a human-mouse chimeric antibody, and a human antibody.

20. The aqueous preparation according to any one of 1 to 17 above, wherein the protein is selected from the group consisting of an anti-IL-6 antibody, an anti-beta-amyloid antibody, an anti-BACE antibody, an anti-EGFR antibody, an anti-PD-1 antibody, an anti-PD-L1 antibody, an anti-HER2 antibody, an anti-PCSK9 antibody, and an anti-TNF-α, antibody.

21. The aqueous preparation according to any one of 1 to 17 above, wherein the protein is a lysosome enzyme, and the lysosome enzyme is selected from the group consisting of α-L-iduronidase, iduronate-2-sulfatase, glucocerebrosidase, β-galactosidase, a GM2-activator protein, β-hexosaminidase A, β-hexosaminidase B, N-acetyl glucosamine-1-phosphotransferase, α-mannosidase, β-mannosidase, galactosylceramidase, saposin C, arylsulfatase A, α-L-fucosidase, aspartylglucosamidase, α-N-acetyl galactosaminidase, acidic sphingomyelinase, α-galactosidase A, β-glucuronidase, heparan N-sulfatase, α-N-acetyl glucosaminidase, acetyl CoAα-glucosaminide N-acetyl transferase, N-acetyl glucosamine-6-sulfate sulfatase, acid ceramidase, amylo-1,6-glucosidase, sialidase, palmitoyl protein thioesterase-1, tripeptidyl peptidase-1, and hyaluronidase-1.

22. The aqueous preparation according to any one of 1 to 17 above, wherein the protein is a fusion protein of an antibody and another protein, and the another protein is selected from the group consisting of a growth hormone, a lysosome enzyme, a cytokine, a lymphokine, a blood clotting factor, an antibody, a fusion protein of an antibody and another protein, granulocyte-macrophage colony-stimulating factor (GM-CSF), granulocyte colony-stimulating factor (G-CSF), macrophage colony-stimulating factor (M-CSF), erythropoietin, darbepoetin, tissue plasminogen activator (t-PA), thrombomodulin, follicle-stimulating hormone, DNaseI, thyroid-stimulating hormone (TSH), nerve growth factor (NGF), ciliary neurotrophic factor (CNTF), glial cell line-derived neurotrophic factor (GDNF), neurotrophin 3, neurotrophin 4/5, neurotrophin 6, neuregulin 1, activin, basic fibroblast growth factor (bFGF), fibroblast growth factor 2 (FGF2), epithelial cell growth factor (EGF), vascular endothelial growth factor (VEGF), interferon α, interferon β, interferon 7, interleukin 6, PD-1, a PD-1 ligand, tumor necrosis factor α, receptor (TNF-α receptor), and an enzyme having activity for decomposing beta-amyloid.

23. The aqueous preparation according to any one of 1 to 17 above, wherein the protein is a fusion protein of an antibody and a lysosome enzyme, and the lysosome enzyme is selected from the group consisting of α-L-iduronidase, iduronate-2-sulfatase, glucocerebrosidase, B galactosidase, a GM2-activator protein, β-hexosaminidase A, β-hexosaminidase B, N-acetyl glucosamine-1-phosphotransferase, α-mannosidase, β-mannosidase, galactosylceramidase, saposin C, arylsulfatase A, α-L-fucosidase, aspartylglucosamidase, α-N-acetyl galactosaminidase, acidic sphingomyelinase, α-galactosidase A, β-glucuronidase, heparan N-sulfatase, α-N-acetyl glucosaminidase, acetyl CoAα-glucosaminide N-acetyl transferase, N-acetyl glucosamine-6-sulfate sulfatase, acid ceramidase, amylo-1,6-glucosidase, sialidase, palmitoyl protein thioesterase-1, tripeptidyl peptidase-1, and hyaluronidase-1.

24. The aqueous preparation according to any one of 1 to 23 above, wherein the aqueous preparation is administered by subcutaneous injection or intramuscular injection.

Effect of Invention

According to the present invention, a pain at the time of injecting a preparation containing a protein as an active ingredient can be reduced.

BRIEF DESCRIPTION OF THE DRAWINGS

FIG. 1 shows an image of a gauge used for letting a test subject to express a pain in Examples 1 and 2.

DESCRIPTION OF EMBODIMENTS

The invention relates to an aqueous preparation in which an active ingredient is a protein. The type of the protein, which is the active ingredient, is not particularly limited, and for example, may be growth hormone, somatomedin (including somatomedins A, B, and C), insulin, glucagon, a lysosome enzyme, a cytokine, a lymphokine, a blood clotting factor (including blood clotting factor VII, blood clotting factor VIII, and blood clotting factor IX), an antibody, a fusion protein of an antibody and another protein, granulocyte-macrophage colony-stimulating factor (GM-CSF), granulocyte colony-stimulating factor (G-CSF), macrophage colony-stimulating factor (M-CSF), erythropoietin, darbepoetin, tissue plasminogen activator (t-PA), thrombomodulin, follicle-stimulating hormone (FSH), gonadotropic hormone-releasing hormone (GnRH), gonadotropin, DNaseI, thyroid-stimulating hormone (TSH), nerve growth factor (NGF), ciliary neurotrophic factor (CNTF), glial cell line-derived neurotrophic factor (GDNF), neurotrophin 3, neurotrophin 4/5, neurotrophin 6, neuregulin 1, activin, basic fibroblast growth factor (bFGF), fibroblast growth factor 2 (FGF2), epithelial cell growth factor (EGF), vascular endothelial growth factor (VEGF), interferon α, interferon S, interferon γ, interleukin 6, PD-1, a PD-1 ligand, tumor necrosis factor α receptor (TNF-α receptor), an enzyme having activity for decomposing beta-amyloid, etanercept, pegvisomant, metreleptin, abatacept, asfotase, and a glucagon-like peptide-1 receptor agonist.

In a case where the active ingredient is the antibody, the species of antibody is not particularly limited, and for example, may be a mouse antibody, a humanized antibody, a human-mouse chimeric antibody, or a human antibody. In addition, an antigen to which the antibody is able to specifically bind is not particularly limited, and for example, may be an anti-IL-6 antibody, an anti-beta-amyloid antibody, an anti-BACE antibody, an anti-EGFR antibody, an anti-PD-1 antibody, an anti-PD-L1 antibody, an anti-HER2 antibody, an anti-PCSK9 antibody, or an anti-TNF-α antibody. In addition, the antibody is not limited to having a basic structure including a total of four polypeptide chains comprising two immunoglobulin light chains and two immunoglobulin heavy chains, and may be a single-chain antibody, Fab, F(ab'), F(ab')$_2$, or an antigen-binding fragment insofar as retaining specificity to a specific antigen.

In a case where the active ingredient is a lysosome enzyme, the type of lysosome enzyme is not particularly limited, and for example, may be α-L-iduronidase, iduronate-2-sulfatase, glucocerebrosidase, S galactosidase, a GM2-activator protein, β-hexosaminidase A, β-hexosaminidase B, N-acetyl glucosamine-1-phosphotransferase, α-mannosidase, β-mannosidase, galactosylceramidase, saposin C, allyl sulfatase A, α-L-fucosidase, aspartylglucosamidase, α-N-acetyl galactosaminidase, acidic sphingomyelinase, α-galactosidase A, β-glucuronidase, heparan N-sulfatase, α-N-acetyl glucosaminidase, acetyl CoAα-glucosaminide N-acetyl transferase, N-acetyl glucosamine-6-sulfate sulfatase, acid ceramidase, amylo-1,6-glucosidase, sialidase, palmitoyl protein thioesterase-1, tripeptidyl peptidase-1, or hyaluronidase-1.

In a case where the active ingredient is the fusion protein of the antibody and another protein, the type of the another protein is not particularly limited, and for example, may be a growth hormone, a lysosome enzyme, cytokine, lymphokine, a blood clotting factor, an antibody, a fusion protein of an antibody and another protein, granulocyte-macrophage colony-stimulating factor (GM-CSF), granulocyte colony-stimulating factor (G-CSF), macrophage colony-stimulating factor (M-CSF), erythropoietin, darbepoetin, tissue plasminogen activator (t-PA), thrombomodulin, follicle-stimulating hormone, DNaseI, thyroid-stimulating hormone (TSH), nerve growth factor (NGF), ciliary neurotrophic factor (CNTF), glial cell line-derived neurotrophic factor (GDNF), neurotrophin 3, neurotrophin 4/5, neurotrophin 6, neuregulin 1, activin, basic fibroblast growth factor (bFGF), fibroblast growth factor 2 (FGF2), epithelial cell growth factor (EGF), vascular endothelial growth factor (VEGF), interferon α, interferon β, interferon γ, interleukin 6, PD-1, a PD-1 ligand, tumor necrosis factor α receptor (TNF-α receptor), or an enzyme having activity for decomposing beta-amyloid.

In a case where the other proteins are the lysosome enzyme, the type of the lysosome enzyme is not particularly limited, and for example, may be α-L-iduronidase, iduronate-2-sulfatase, glucocerebrosidase, $ galactosidase, a GM2-activator protein, β-hexosaminidase A, β-hexosaminidase B, N-acetyl glucosamine-1-phosphotransferase, α-mannosidase, β-mannosidase, galactosylceramidase, saposin C, arylsulfatase A, α-L-fucosidase, aspartylglucosamidase, α-N-acetyl galactosaminidase, acidic sphingomyelinase, α-galactosidase A, β-glucuronidase, heparan N-sulfatase, α-N-acetyl glucosaminidase, acetyl CoAα-glucosaminide N-acetyl transferase, N-acetyl glucosamine-6-sulfate sulfatase, acid ceramidase, amylo-1,6-glucosidase, sialidase, palmitoyl protein thioesterase-1, tripeptidyl peptidase-1, or hyaluronidase-1.

The species of protein that is contained in the aqueous preparation as the active ingredient is not particularly limited, but is preferably a human protein. The protein can be produced as a recombinant protein by using a gene recombination technology. The recombinant protein, for example, can be produced by incorporating a gene encoding the protein into an expression vector, transforming a mammal cell (for example, a CHO cell derived from a Chinese hamster ovary cell), E. coli cell, or the like by the expression vector, and culturing the transformed cell.

In the present invention, when referred to as "growth hormone", it may be in particular a human growth hormone, but not limited this, and also may include a growth hormone of any one of mammals including a domestic livestock such as a cow and a horse and a pet such as a dog and a cat. In addition, the "growth hormone" also includes a growth hormone analog in which one or a plurality of amino-acid residues configuring the growth hormone are substituted, deleted, or inserted.

In the present invention, the growth hormone can be produced by using the gene recombination technology. A method for producing a biologically active growth hormone by incorporating the growth hormone gene in an expression vector, transforming a mammalian cell (for example, a CHO cell derived from a Chinese hamster ovary cell) or E. coli with the expression vector, and culturing the transformed cell is well known to a person skilled in the art (US 2010/0227819, U.S. Pat. No. 4,342,832, and the like).

In the present invention, the concentration of the protein contained in the aqueous preparation is not particularly limited. However, the concentration is preferably 1 to 50 mg/mL, more preferably 1 to 10 mg/mL, and even more preferably 2 to 8 mg/mL. A preferred concentration of the protein, for example, is 4 mg/mL or 8 mg/mL. Such a concentration is particularly preferable in a case where the protein is the growth hormone.

The aqueous preparation of the protein of the invention contains a phosphate buffer as a buffer. The concentration of the phosphate buffer contained in the aqueous preparation is preferably 1 to 20 mM, more preferably 5 to 16 mM, even more preferably 8 to 15 mM, and still even more preferably 8 to 12 mM. For example, the final concentration in the aqueous preparation is adjusted to 10 mM, 11 mM, or 12 mM. The pH of the aqueous preparation containing the buffer is preferably 5.5 to 7.2, more preferably 6.0 to 6.4, even more preferably 6.0 to 6.3, and particularly preferably 6.2.

The aqueous preparation of the protein of the present invention further contains a non-ionic surfactant. As the non-ionic surfactant contained in the aqueous preparation, polysorbate, poloxamer, or the like may be used alone or in combination thereof. Polysorbate 20 and polysorbate 80 are particularly preferable as the polysorbate, and poloxamer 188 (polyoxyethylene (160) polyoxypropylene (30) glycol) is particularly preferable as the poloxamer. Further, the concentration of the non-ionic surfactant contained in the aqueous preparation is preferably 1 to 10 mg/mL, more preferably 1 to 5 mg/mL, even more preferably 1 to 3 mg/mL, still even more preferably 1.5 to 2.5 mg/mL, and still even more preferably 1.8 to 2.2 mg/mL, and for example, may be adjusted to 2 mg/mL. In a case where poloxamer 188 (polyoxyethylene (160) polyoxypropylene (30) glycol) is used as the non-ionic surfactant, the concentration in the aqueous preparation is preferably 1 to 10 mg/mL, more preferably 1 to 5 mg/mL, even more preferably 1 to 3 mg/mL, still even more preferably 1.5 to 2.5 mg/mL, and is still even more preferably 1.8 to 2.2 mg/mL, and for example, may be adjusted to 2 mg/mL.

The aqueous preparation of the protein may be assumed to be not used only once but used repeatedly after opening without making it disposable. In this case, it is desirable that deterioration of quality due to the contamination of bacteria during the repeated use have to be prevented. Accordingly, the aqueous preparation of the protein of the present invention may contain an antiseptic agent. The antiseptic agent containing in the aqueous preparation is not particularly limited insofar as being pharmaceutically suitable, but benzyl alcohol, phenol, a benzoic acid, or a mixture thereof may be preferably used.

In a case where phenol is used as the antiseptic agent, the concentration in the aqueous preparation is preferably 1 to 10 mg/mL, more preferably 2.5 to 4.0 mg/mL, and even more preferably 2.8 to 3.8 mg/mL, and for example, is 3.3 mg/mL. In a case where benzyl alcohol is used as the antiseptic agent, the concentration in the aqueous preparation is preferably 2 to 20 mg/mL, more preferably 7 to 12 mg/mL, and even more preferably 8 to 10 mg/mL, and for example, is 9 mg/mL. In a case where a benzoic acid is used as the antiseptic agent, the concentration in the aqueous preparation is preferably 1 to 20 mg/mL.

The aqueous preparation of the protein of the present invention may further contain an isotonic agent. The isotonic agent contained in the aqueous preparation is not particularly limited insofar as being pharmaceutically suitable, but a sugar alcohol, a neutral salt, or a mixture thereof can be preferably used. A preferred example of a sugar alcohol includes D-mannitol, and a preferred example of a neutral salt includes sodium chloride. In a case where D-mannitol is used as the isotonic agent, the concentration in the aqueous preparation is preferably 35 to 70 mg/mL, and more preferably 35 to 45 mg/mL, and for example, is 40 mg/mL. In a case where sodium chloride is used as the isotonic agent, the concentration in the aqueous preparation is preferably 5.5 to 11.5 mg/mL, more preferably 5.5 to 7.5 mg/mL, and for example, is 6.5 mg/mL. However, the concentration of the isotonic agent is not limited thereto, and can be adjusted in a relationship with respect to the concentration of the other ingredients in the aqueous preparation as needed. In general, the concentration of the isotonic agent is adjusted such that the osmotic pressure ratio of the aqueous preparation is 0.9 to 1.6, and more preferably 0.9 to 1.1 with reference to the osmotic pressure of the physiological saline. In the present invention, when referred to as "an osmotic pressure", it means an osmotic pressure with reference to the osmotic pressure of the physiological saline.

Preferred examples of the aqueous preparation of the protein of the invention are as follows.

Preferred Example 1

An aqueous preparation, containing: 1 to 50 mg/mL of a protein; 5 to 16 mM of a phosphate buffer; 1.8 to 2.2 mg/mL of poloxamer 188; 2.8 to 3.8 mg/mL of phenol; and 35 to 45 mg/mL of D-mannitol, in which pH is 6.0 to 6.4. However, in order to adjust the pH, phosphate and/or sodium hydroxide may be further added, and the concentration of D-mannitol may increase or decrease such that an osmotic pressure ratio is adjusted to 0.9 to 1.1. In addition, 8 to 10 mg/mL of benzyl alcohol may be added instead of phenol.

Preferred Example 2

An aqueous preparation, containing: 1 to 10 mg/mL of a protein; 8 to 15 mM of a phosphate buffer; 1.8 to 2.2 mg/mL of poloxamer 188; 2.8 to 3.8 mg/mL of phenol; and 35 to 45 mg/mL of D-mannitol, in which pH is 6.0 to 6.4. However, in order to adjust the pH, phosphate and/or sodium hydroxide may be further added, and the concentration of D-mannitol may increase and decrease such that an osmotic pressure ratio is adjusted to 0.9 to 1.1. In addition, 8 to 10 mg/mL of benzyl alcohol may be added instead of phenol.

Preferred Example 3

An aqueous preparation, containing: 2 to 8 mg/mL of a protein; 10 mM of a phosphate buffer; 2 mg/mL of poloxamer 188; 3.3 mg/mL of phenol; and 40 mg/mL of D-mannitol, in which pH is 6.2. However, in order to adjust the pH, phosphate and/or sodium hydroxide may be further added, and the concentration of D-mannitol may increase and decrease such that an osmotic pressure ratio is adjusted to 0.9 to 1.1. In addition, 8 to 10 mg/mL of benzyl alcohol may be added instead of phenol.

In the aqueous preparation of the protein of the present invention, the protein is not degraded even if it is stored long-term at 2 to 8° C. Here, when referred to as "the degradation of the protein", it means that a quantitative value of the protein becomes 98% or less, for example, 95% or less, with reference to the quantitative value of the aqueous preparation immediately after filling a vial or an injector as a pharmaceutical preparation. Further, in a case where the activity originally possessed by the protein becomes 98% or less, for example, 95% or less, with reference to the activity immediately after filling a vial or an injector as a pharmaceutical preparation, it is also defined that the protein is degraded.

A time period in which the protein can be stored without degradation is preferably 18 months or more, more preferably 24 months or more, even more preferably 30 months or more, and still even more preferably 36 months.

The aqueous preparation of the protein of the invention is administered to a patient by intramuscular injection, subcutaneous injection, or the like. In a case where the injection is accompanied by a pain, medication compliance of the patient decreases, and thus, a therapeutic effect may not be sufficiently obtained. By using the aqueous preparation of the present invention, the pain that is felt by the patient during the injection can be reduced, and thus, the medication compliance of the patient increases, and the patient does not avoid the medication.

The pain that is felt during the injection is subjective, therefore a visual analogue scale (VAS) is generally used as a method for objectively evaluating the pain. VAS is a method generally including the following steps. (1) presenting a straight line of 100 mm in which a left end indicates painlessness and a right end indicates the worst pain that can be imagined to a test subject; (2) letting the test subject to indicate the pain which is felt during the injection on the straight line; and (3) quantifying the pain indicated by the test subject and counting up the quantified pain.

As another method for objectively evaluating the pain, a numerical rating scale (NRS) is known. The numerical rating scale is a method generally including the following steps. (1) presenting a straight line divided into 11 stages from painlessness to the worst pain to a test subject; (2) expressing the pain that is felt by the test subject by using a numerical value on the straight line; and (3) counting up the numerical value.

As another method for objectively evaluating the pain, a faces pain scale (a face scale) is known. In VAS and NRS, the pain that is felt by the test subject is expressed by using the numerical value on a gauge, but in the face scale, the pain that is felt by the test subject is expressed by using a human facial expression according to the pain on the gauge.

A method in which VAS, NRS, and the face scale are suitably combined, or a method in which VAS, NRS, and the face scale are modified may also be used as the method for objectively evaluating the pain, but the method is not limited thereto.

The aqueous preparation of the present invention is the preparation having, for example, a feature that when the preparation is subcutaneously injected to the test subject, the pain felt by the test subject is weaker than the pain which is felt by the test subject when a physiological saline is injected if the pains are evaluated by using the method for objectively evaluating the pain above.

An embodiment where the protein contained in the aqueous preparation is the growth hormone is described below in detail.

In the present invention, the concentration of the growth hormone contained in the aqueous preparation is not particularly limited. However, the concentration is preferably 1 to 12 mg/mL, and more preferably 2 to 8 mg/mL. A preferred concentration of the growth hormone, for example, is 4 mg/mL or 8 mg/mL.

The aqueous preparation of the growth hormone of the present invention contains a phosphate buffer as a buffer. The concentration of the phosphate buffer contained in the aqueous preparation is preferably 1 to 20 mM, more preferably 5 to 16 mM, even more preferably 8 to 15 mM, and still even more preferably 8 to 12 mM. For example, the final concentration in the aqueous preparation is adjusted to 10 mM, 11 mM, or 12 mM. The pH of the aqueous preparation containing the buffer is preferably 5.5 to 7.2, more preferably 6.0 to 6.4, even more preferably 6.0 to 6.3, still even more preferably 6.0 to 6.2, and is particularly 6.2.

The aqueous preparation of the growth hormone of the present invention further contains a non-ionic surfactant. As the non-ionic surfactant contained in the aqueous preparation, polysorbate, poloxamer, or the like may be used alone or in combination thereof. Polysorbate 20 and polysorbate 80 are particularly preferable as polysorbate, and poloxamer 188 (polyoxyethylene (160) polyoxypropylene (30) glycol) is particularly preferable as poloxamer. In addition, the concentration of the non-ionic surfactant contained in the aqueous preparation is preferably 1 to 10 mg/mL, more preferably 1 to 5 mg/mL, even more preferably 1 to 3 mg/mL, still even more preferably 1.5 to 2.5 mg/mL, and further even more preferably 1.8 to 2.2 mg/mL, and for example, is adjusted to 2 mg/mL. In a case where poloxamer 188 (polyoxyethylene (160) polyoxypropylene (30) glycol) is used as the non-ionic surfactant, the concentration in the aqueous preparation is preferably 1 to 5 mg/mL, more preferably 1 to 3 mg/mL, even more preferably 1.5 to 2.5 mg/mL, and still even more preferably 1.8 to 2.2 mg/mL, and for example, is adjusted to 2 mg/mL.

The aqueous preparation of growth hormone may be assumed to be not used only once but used repeatedly after opening without making it disposable. In this case, it is desirable that deterioration of quality due to the contamination of bacteria during the repeated use have to be prevented. Accordingly, the aqueous preparation of growth hormone of the present invention may contain an antiseptic agent. The antiseptic agent containing in the aqueous preparation is not particularly limited insofar as being pharmaceutically suitable, but benzyl alcohol, phenol, a benzoic acid, or a mixture thereof may be preferably used.

In a case where phenol is used as the antiseptic agent, the concentration in the aqueous preparation is preferably 1 to 10 mg/mL, more preferably 2.5 to 4.0 mg/mL, and even more preferably 2.8 to 3.8 mg/mL, and for example, is 3.3 mg/mL. In a case where benzyl alcohol is used as the antiseptic agent, the concentration in the aqueous preparation is preferably 2 to 20 mg/mL, more preferably 7 to 12 mg/mL, and even more preferably 8 to 10 mg/mL, and for example, is 9 mg/mL. In a case where a benzoic acid is used as the antiseptic agent, the concentration in the aqueous preparation is preferably 1 to 20 mg/mL.

The aqueous preparation of the growth hormone of the present invention is further capable of containing an isotonic agent. The isotonic agent contained in the aqueous preparation is not particularly limited insofar as being pharmaceutically suitable, but a sugar alcohol, a neutral salt, or a mixture thereof may be preferably used. A preferred example of a sugar alcohol includes D-mannitol, and a preferred example of a neutral salt includes sodium chloride. In a case where D-mannitol is used as the isotonic agent, the concentration in the aqueous preparation is preferably 35 to 70 mg/mL, and more preferably 35 to 45 mg/mL, and for example, is 40 mg/mL. In a case where sodium chloride is used as the isotonic agent, the concentration in the aqueous preparation is preferably 25 to 35 mg/mL, and more preferably 5.5 to 7.5 mg/mL, and for example, is 6.5 mg/mL. However, the concentration of the isotonic agent is not limited thereto, and can be suitably adjusted in a relationship with respect to the concentration of the other ingredients in the aqueous preparation. In general, the concentration of the isotonic agent is adjusted such that the osmotic pressure ratio of the aqueous preparation is 0.9 to 1.6, and more preferably 0.9 to 1.1 with reference to the osmotic pressure of the physiological saline.

Preferred examples of the aqueous preparation of the growth hormone of the present invention are as follows.

Preferred Example 1'

An aqueous preparation, containing: 1 to 12 mg/mL of a growth hormone; 5 to 16 mM of a phosphate buffer; 1.8 to 2.2 mg/mL of poloxamer 188; 2.8 to 3.8 mg/mL of phenol; and 35 to 45 mg/mL of D-mannitol, in which pH is 6.0 to 6.3. However, in order to adjust the pH, phosphate and/or sodium hydroxide may be further added, and the concentration of D-mannitol may increase and decrease such that an osmotic pressure ratio is adjusted to 0.9 to 1.1. In addition, 8 to 10 mg/mL of benzyl alcohol may be added instead of phenol.

Preferred Example 2'

An aqueous preparation, containing: 4 to 8 mg/mL of a growth hormone; 5 to 16 mM of a phosphate buffer; 1.8 to 2.2 mg/mL of poloxamer 188; 2.8 to 3.8 mg/mL of phenol; and 35 to 45 mg/mL of D-mannitol, in which pH is 6.0 to 6.3. However, in order to adjust the pH, phosphate and/or sodium hydroxide may be further added, and the concentration of D-mannitol may increase and decrease such that an osmotic pressure ratio is adjusted to 0.9 to 1.1. In addition, 8 to 10 mg/mL of benzyl alcohol may be added instead of phenol.

Preferred Example 3'

An aqueous preparation, containing: 4 to 8 mg/mL of a growth hormone; 8 to 12 mM of a phosphate buffer; 2 mg/mL of poloxamer 188; 3.3 mg/mL of phenol; and 40 mg/mL of D-mannitol, in which pH is 6.2. However, in order to adjust the pH, phosphate and/or sodium hydroxide may be further added, and the concentration of D-mannitol may increase and decrease such that an osmotic pressure ratio is adjusted to 0.9 to 1.1. In addition, 9 mg/mL of benzyl alcohol may be added instead of phenol.

Preferred Example 4'

An aqueous preparation, containing: 4 mg/mL or 8 mg/mL of a growth hormone; 10 mM of a phosphate buffer; 2 mg/mL of poloxamer 188; 3.3 mg/mL of phenol; and 40 mg/mL of D-mannitol, in which pH is 6.2. However, in order to adjust the pH, phosphate and/or sodium hydroxide may be further added, and the concentration of D-mannitol may increase and decrease such that an osmotic pressure ratio is adjusted to 0.9 to 1.1. In addition, 9 mg/mL of benzyl alcohol may be added instead of phenol.

Preferred Example 5'

An aqueous preparation, containing: 4 mg/mL or 8 mg/mL of a growth hormone; 10 mM of a phosphate buffer; 2 mg/mL of poloxamer 188; 3.3 mg/mL of phenol; and 40 mg/mL of D-mannitol, in which pH is 6.2. However, in order to adjust the pH, phosphate and/or sodium hydroxide may be further added, and the concentration of D-mannitol may increase and decrease such that an osmotic pressure ratio is adjusted to 0.9 to 1.1. In addition, 9 mg/mL of benzyl alcohol may be added instead of phenol.

The aqueous preparation of the growth hormone of the present invention may be a preparation filled in a vial, or may be a prefilled syringe-type or cartridge-type preparation filled in advance in an injector. In a case where the aqueous preparation is the prefilled syringe-type or cartridge-type preparation, in general, the amount of liquid filled in one injector is adjusted to 1 to 2 mL, and for example, one injector is filled with the liquid such that an indication amount is 1.5 mL.

Immediately after the growth hormone is prepared as the aqueous preparation, most of the growth hormone exists as a monomer in an aqueous solution. However, in a case where the growth hormone is stored as the aqueous preparation, a dimer is generated over time, and thus, the ratio of the growth hormone existing as the monomer decreases. In addition, a quantitative value of the growth hormone also decreases over time.

In the aqueous preparation of growth hormone of the present invention, the protein is not degraded even if it is stored long-term at 2 to 8° C. Here, when referred to as "the degradation of growth hormone", it means that a ratio of growth hormone existing as monomer becomes 98% or less, for example, 95% or less. Further, in a case where the activity originally possessed by growth hormone becomes 98% or less, for example, 95% or less, with reference to the activity immediately after filling a vial or an injector as a pharmaceutical preparation, it is also defined that growth hormone is degraded.

A time period in which growth hormone can be stored without degradation is preferably 18 months or more, more preferably 24 months or more, even more preferably 30 months or more, and still even more preferably 36 months.

The aqueous preparation of the growth hormone of the present invention is administered to a patient by intramuscular injection or subcutaneous injection. It is assumed that the administration to the patient is performed by not only a medical doctor but also by the patient or a parent of the patient. In such a type of pharmacological agent, the patient or the parent of the patient is required to comply with an administration schedule, and in a case where the injection is accompanied by a pain, medication compliance of the patient should decrease, and thus, a therapeutic effect may not be sufficiently obtained. By using the aqueous preparation of growth hormone of the present invention, the pain that is felt by the patient during the injection can be reduced, and thus, the medication compliance of the patient is improved, resulting in that all the patients can receive the expected therapeutic benefit.

The pain that is felt during the injection is subjective, therefore a visual analogue scale (VAS) is generally used as a method for objectively evaluating the pain. VAS is a method generally including the following steps: (1) presenting a horizontal straight line in which a left end indicates painlessness and a right end indicates the worst pain that can be imagined; (2) letting the test subject to indicate the pain which is felt on the straight line; and (3) quantifying the pain indicated by the test subject and counting up the quantified pain. The length of the line is 100 mm in general.

As another method for objectively evaluating the pain, a numerical rating scale (NRS) is known. The numerical rating scale is a method generally including the following steps. (1) presenting a straight line divided into 11 stages from painlessness to the worst pain to a test subject; (2) expressing the pain that is felt by the test subject by using a numerical value on the straight line; and (3) counting up the numerical value.

As another method for objectively evaluating the pain, a faces pain scale (a face scale) is known. In VAS and NRS, the pain that is felt by the test subject is expressed by using the numerical value on a gauge, but in the face scale, the pain that is felt by the test subject is expressed by using a human facial expression according to the pain on the gauge.

A method in which VAS, NRS, and the face scale are suitably combined, or a method in which VAS, NRS, and the face scale are modified may also be used as the method for objectively evaluating the pain, but the method is not limited thereto.

The aqueous preparation of growth hormone of the present invention is the preparation having, for example, a feature that when the preparation is subcutaneously injected to the test subject, the pain felt by the test subject is weaker than the pain which is felt by the test subject when a physiological saline is injected if the pains are evaluated by using the method for objectively evaluating the pain above.

EXAMPLES

While the present invention will be described in further detail below referring to examples, it is not intended that the present invention be limited to the examples.

[Example 1] Evaluation of Pain of Aqueous Preparation (1)

Aqueous preparations of Formulation 1 and Formulation 2 containing a phosphate buffer and D-mannitol, as shown in Table 1, were prepared. Concentrations of the phosphate buffer in Formulation 1 and Formulation 2 are 20 mM and 50 mM, respectively. In both of formulations, osmotic pressure ratios are 1.0 to 1.1.

TABLE 1

Table 1 Compositions of aqueous preparations (Formulation 1 and Formulation 2)

| Ingredients | Formulation 1 | Formulation 2 |
|---|---|---|
| Sodium dihydrogen phosphate hydrate | 16.3 mM | 40.75 mM |
| Disodium hydrogen phosphate hydrate | 3.7 mM | 9.25 mM |
| D-mannitol | 246 mM | 186 mM |
| | (44.8 mg/mL) | (33.9 mg/mL) |
| pH | 6.2 | 6.1 |

The evaluation of the pain was implemented by using a gauge illustrated in FIG. 1 in which a schematic facial expression expressing a pain is represented on a gauge. By using the gauge, the pain was digitized in 10 stages in which "Not Feeling Any Pain" was set to 1 and "Worst Possible Pain" was set to 10. Three test subjects were recruited in the test, a male in twenties, a male in forties, and a male in fifties. Formulation 1 in which the concentration of the phosphate buffer was 20 mM, Formulation 2 in which the concentration of the phosphate buffer was 50 mM, and a physiological saline were each administered to the test subjects once, avoiding to administer to a same part. The administration was implemented such that the solution to be administered was not capable of being discriminated by the test subject. All the solution was subcutaneously administered at a dose of 125 µL to the thigh or the arm of the test subject by using an injection needle (BD micro-fine plus 31G×5 mm, manufactured by Becton, Dickinson and Company). The gauge illustrated in FIG. 1 was presented to the test subject immediately after the administration, and the most suitable expression corresponding to an injection pain was selected from the schematic facial expression presented on the gauge. The numerical value of the selected pain was counted up, and an average value thereof was calculated as the score of the pain. The results were that the score of the pain was 3.0 in Formulation 1, 3.7 in Formulation 2, and 2.0 in the physiological saline. These results indicate that the pain caused by the injection of the aqueous preparation can be reduced by decreasing the concentration of the phosphate buffer. In consideration of the safety of the test subject, the test was performed by using an aqueous preparation not containing a protein ingredient.

[Example 2] Evaluation of Pain of Aqueous Preparation (2)

Aqueous preparations of Formulation 3 to Formulation 5 containing a phosphate buffer, D-mannitol, poloxamer 188, and phenol, as shown in Table 2, were prepared. Only in Formulation 5, a suitable amount of sodium hydroxide was added in order to adjust the pH. The concentrations of the phosphate buffer of Formulation 3, Formulation 4, and Formulation 5 are 10 mM, 20 mM, and 50 mM, respectively. The osmotic pressure ratios are 1.0 to 1.1 for all the solutions.

TABLE 2

Table 2 Compositions of aqueous preparations (Formulation 3 to Formulation 5)

| Ingredients | Formulation 3 | Formulation 4 | Formulation 5 |
| --- | --- | --- | --- |
| Sodium dihydrogen phosphate hydrate | 8.58 mM | 12.72 mM | 35 mM |
| Disodium hydrogen phosphate hydrate | 1.42 mM | 2.28 mM | 15 mM |
| D-mannitol | 230.6 mM (42 mg/mL) | 219.6 mM (40 mg/mL) | 146.4 mM (26.7 mg/mL) |
| Poloxamer 188 | 2 mg/mL | 2 mg/mL | 2 mg/mL |
| Phenol | 35.42 mM (3.33 mg/mL) | 35.42 mM (3.33 mg/mL) | 35.42 mM (3.33 mg/mL) |
| Sodium hydroxide | — | — | Properly |
| pH | 6.1 | 6.2 | 6.4 |

Three test subjects were recruited in the test, a male in twenties, a male in forties, and a male in fifties. Formulation 3 in which the concentration of the phosphate buffer was 10 mM, Formulation 4 in which the concentration of the phosphate buffer was 15 mM, Formulation 5 in which the concentration of the phosphate buffer was 50 mM, and a physiological saline were each administered to the test subjects once, avoiding to administer to a same part. The administration was implemented such that the solution to be administered was not capable of being discriminated by the test subject. All the solution was subcutaneously administered at a dose of 125 µL to the thigh or the arm of the test subject by using an injection needle (BD micro-fine plus 31G×5 mm, manufactured by Becton, Dickinson and Company). And then the score of the pain of each of the formulations was calculated by the same way as described in Example 1. The results were that the score of the pain was 2.0 in Formulation 3, 2.0 in Formulation 4, 4.3 in Formulation 5, and 2.7 in the physiological saline. These results indicate that the injection pain caused by the aqueous preparation can be dramatically reduced by setting the concentration of the phosphate buffer to be 15 mM or less. In particular, it is surprising that the pain caused by the injection can be reduced by setting the concentration of the phosphate buffer to 15 mM or less, if compared to the pain caused by the physiological saline. In consideration of the safety of the test subject, the test was performed by using an aqueous preparation not containing a protein ingredient.

[Example 3] Evaluation of Pain of Aqueous Preparation (3)

Aqueous preparations of Formulation 6 to Formulation 7 containing a phosphate buffer, D-mannitol, poloxamer 188, and phenol, as shown in Table 3 were prepared. Only in Formulation 6, a suitable amount of sodium hydroxide was added in order to adjust the pH. The concentrations of the phosphate buffers of Formulation 6 and Formulation 7 are 10 mM and 50 mM, respectively. The osmotic pressure ratios are 1.0 to 1.1 for all the solutions.

TABLE 3

Table 3 Compositions of aqueous preparations (Formulation 6 to Formulation 7)

| Ingredients | Formulation 6 | Formulation 7 |
| --- | --- | --- |
| Sodium dihydrogen phosphate hydrate | 10 mM | 43.2 mM |
| Disodium hydrogen phosphate hydrate | 0 mM | 6.8 mM |
| D-mannitol | 219.6 mM (40 mg/mL) | 146.4 mM (26.7 mg/mL) |
| Poloxamer 188 | 2 mg/mL | 2 mg/mL |
| Phenol | 35.42 mM (3.33 mg/mL) | 35.42 mM (3.33 mg/mL) |
| Sodium hydroxide | Properly | — |
| pH | 6.2 | 6.2 |

The pains induced by formulation 6 in which the concentration of the phosphate buffer was 10 mM, Formulation 7 in which the concentration of the phosphate buffer was 50 mM, and a physiological saline were compared, with thirty one test subjects were recruited (the test subjects include male and female at age 20s to 70s). Each of formulations were administered to the test subjects once, avoiding to administer to a same part. The administration was implemented such that the solution to be administered was not capable of being discriminated by the test subject. All the solution was subcutaneously administered at a dose of 125 µL to the thigh or the arm of the test subject by using an injection needle (BD micro-fine plus 31G×5 mm, manufactured by Becton, Dickinson and Company). And the score of the pain caused by each of the formulations was calculated by the same way as described in Example 1. The results were that the score of the pain was 2.6 in Formulation 6, 4.9 in Formulation 7, and 2.7 in the physiological saline. These results indicate that the pain caused by injection can be reduced by reducing the concentration of the phosphate buffer and that the pain caused by the injection can be reduced by setting the concentration of the phosphate buffer to be 10 mM or less, if compared to the pain that caused by the physiological saline. In consideration of the safety of the test subject, the test was performed by using an aqueous preparation not containing a protein ingredient.

[Example 4] Evaluation of Stability of Aqueous Preparation of Human Growth Hormone (1)

Four types of aqueous preparations of growth hormones were prepared, GH Formulation 1 to GH Formulation 4 as shown in Table 4. The concentrations of phosphate buffer of GH Formulation 1 and GH Formulation 2 are 50 mM and 16 mM, respectively. The compositions of GH Formulation 3 and GH Formulation 4 differ only in growth hormone concentration but the concentrations of the phosphate buffer are both 10 mM.

TABLE 4

Table 4 Compositions of aqueous preparations of GH (GH Formulation 1 to GH Formulation 4)

| Ingredients | GH Formulation 1 | GH Formulation 2 | GH Formulation 3 | GH Formulation 4 |
|---|---|---|---|---|
| Growth hormone | 8 mg/mL | 8 mg/mL | 4 mg/mL | 8 mg/mL |
| Phosphate buffer | 50 mM | 16 mM | 10 mM | 10 mM |
| D-mannitol | 146.4 mM (26.67 mg/mL) | 219.6 mM (40 mg/mL) | 219.6 mM (40 mg/mL) | 219.6 mM (40 mg/mL) |
| Poloxamer 188 | 2 mg/mL | 2 mg/mL | 2 mg/mL | 2 mg/mL |
| Phenol | 35.42 mM (3.33 mg/mL) | 35.42 mM (3.33 mg/mL) | 35.42 mM (3.33 mg/mL) | 35.42 mM (3.33 mg/mL) |
| Sodium hydroxide or Phosphate | — | Properly | Properly | Properly |
| pH | 6.0~6.4 | 6.0~6.4 | 6.0~6.4 | 6.0~6.4 |
| Osmotic pressure ratio | 0.9~1.1 | 0.9~1.1 | 0.9~1.1 | 0.9~1.1 |

A glass cartridge was filled with 1.5 mL of each of the aqueous preparations of GH Formulation 1 to GH Formulation 4, and was stored in a dark place at a temperature of 2 to 8° C. (a long-term storage test) or was stored in a dark place at a temperature of 25° C. (an accelerated test) In a storage period, the pH, a monomer (%), and quantity (%) of the solution were continuously obtained. The monomer (%) and the quantity (%) were obtained by the method described in Example 6.

The results of the evaluation of the stability of GH Formulation 1 in which the concentration of the phosphate buffer is 50 mM are shown in Table 5. In the long-term storage test, the pH, the monomer (%), and the quantity (%) were measured at the start time of the storage, 3 months after, 6 months after, 9 months after, 12 months after, 18 months after, and 24 months after the start time of the storage. In the storage period of the long-term storage test, the pH and the quantity (%) were hardly changed, and the monomer (%) was also retained to be greater than or equal to 99%. In the accelerated test, the pH, the monomer (%), and the quantity (%) were measured 1 month after, 2 months after, and 3 months after the start time of the storage. In the storage period of the accelerated test, the pH and the quantity (%) were hardly changed, and the monomer (%) was also retained to be greater than or equal to 98%. These results indicate that GH Formulation 1 is stable in a dark place at a temperature of 2 to 8° C. for at least 24 months. In addition, the values obtained in the long-term storage test suggest that in a case where standard values of a monomer (%) and the quantity (%) were set to be greater than or equal to 98% and greater than or equal to 100%, respectively, GH Formulation 1 was expected to satisfy the standard value even 36 months after the start time of the storage, when being stored in a dark place at a temperature of 2 to 8° C.

TABLE 5

Table 5 Stability of aqueous preparation (GH Formulation 1) (Reference Example)

| Categories | Time point | pH | Monomer (%) | Quantity (%) |
|---|---|---|---|---|
| | Starting point | 6.21 | >99.5 | 101.4 |
| Long-term Storage Test (2~8° C.) | 3 months | 6.22 | 99.53 | 101.3 |
| | 6 months | 6.23 | 99.48 | 102.5 |
| | 9 months | 6.23 | 99.45 | 101.9 |

TABLE 5-continued

Table 5 Stability of aqueous preparation (GH Formulation 1) (Reference Example)

| Categories | Time point | pH | Monomer (%) | Quantity (%) |
|---|---|---|---|---|
| | Starting point | 6.21 | >99.5 | 101.4 |
| | 12 months | 6.21 | 99.43 | 102.2 |
| | 18 months | 6.22 | 99.49 | 102.8 |
| | 24 months | 6.22 | 99.42 | 101.7 |
| Accelerated Test (25° C.) | 1 month | 6.23 | 99.12 | 100.8 |
| | 2 months | 6.19 | 99.01 | 101.6 |
| | 3 months | 6.22 | 98.87 | 103.0 |

The results of the evaluation of the stability of GH Formulation 2 in which the concentration of the phosphate buffer is 16 mM are shown in Table 6. In the long-term storage test, the pH, the monomer (%), and the quantity (%) were measured at the start time of the storage, 1 month after and 3 months after the start time of the storage. In the storage period of the long-term storage test, the pH, the monomer (%), and the quantity (%) were hardly changed, and had values equivalent to those of GH Formulation 1. In the accelerated test, the pH, the monomer (%), and the quantity (%) were measured 1 month after, 2 months after, and 3 months after the start time of the storage. In the storage period of the accelerated test, the pH, the monomer (%), and the quantity (%) were hardly changed, and had values equivalent to those of GH Formulation 1. These results indicate that GH Formulation 2 has stability equivalent to that of GH Formulation 1, and GH Formulation 2 is expected to be stable in a dark place at a temperature of 2 to 8° C. for at least 24 months. In addition, these results suggest that in a case where standard values of a monomer (%) and the quantity (%) were set to be greater than or equal to 98% and greater than or equal to 100%, respectively, GH Formulation 1 was expected to satisfy the standard value even 36 months after the start time of the storage, when being stored in a dark place at a temperature of 2 to 8° C.

TABLE 6

Table 6 Stability of aqueous preparation (GF Formulation 2)

| Categories | Time point Starting point | pH 6.17 | Monomer (%) 99.65 | Quantity (%) 105 |
|---|---|---|---|---|
| Long-term Storage Test (2~8° C.) | 1 month | 6.21 | 99.66 | 106 |
|  | 3 months | 6.20 | 99.67 | 106 |
| Accelerated Test (25° C.) | 1 month | 6.21 | 99.40 | 106 |
|  | 2 months | 6.21 | 99.22 | 104 |
|  | 3 months | 6.21 | 99.04 | 108 |

The results of the evaluation of the stability of GH Formulation 3 and GH Formulation 4, in which the concentration of the phosphate buffer is 10 mM, are shown in Table 7 and Table 8, respectively. In the long-term storage test, the pH, the monomer (%), and the quantity (%) were measured at the start time of the storage, and approximately 1 month (in 4 weeks) after the start time of the storage. In both formulations, in the storage period of the long-term storage test, the pH, the monomer (%), and the quantity (%) were hardly changed, and had values substantially identical to those of GH Formulation 1. In the accelerated test, the pH, the monomer (%), and the quantity (%) were measured in approximately 1 month (in 4 weeks) after the start time of the storage. In both formulation, in the storage period of the accelerated test, the pH, the monomer (%), and the quantity (%) were hardly changed, and had values substantially identical to those of GH Formulation 1. These results indicate that GH Formulations 3 and 4 have stability equivalent to that of GH Formulation 1, and GH Formulations 3 and 4 are expected to be stable in a dark place at a temperature of 2 to 8° C. for at least 24 months. In addition, in a case where standard values of the monomer amount (%) and the quantity (%) are set to be greater than or equal to 98% and greater than or equal to 100%, respectively, GH Formulations 3 and 4 are expected to satisfy the standard value even 36 months after the start time of the storage, when being stored in a dark place at a temperature of 2 to 8° C.

TABLE 7

Table 7 Stability of aqueous preparation (GF Formulation 3)

| Categories | Time point Starting point | pH 6.22 | Monomer (%) 99.70 | Quantity (%) 101 |
|---|---|---|---|---|
| Long-term Storage Test (2~8° C.) | 4 weeks | 6.22 | 99.68 | 103 |
| Accelerated Test (25° C.) | 4 weeks | 6.21 | 99.61 | 102 |

TABLE 8

Table 8 Stability of aqueous preparation (GH Formulation 4)

| Categories | Time point Starting point | pH 6.23 | Monomer (%) 99.68 | Quantity (%) 101 |
|---|---|---|---|---|
| Long-Term Storage Test (2~8° C.) | 4 weeks | 6.22 | 99.69 | 102 |
| Accelerated Test (25° C.) | 4 weeks | 6.22 | 99.50 | 104 |

[Example 5] Evaluation of Stability of Aqueous Preparation of Human Growth Hormone (2)

Long-term storage test until 9 months after the start time of the storage and accelerated test until 3 months after the start time of the storage were performed for GH Formulation 3 and GH Formulation 4 in both of which the concentration of the phosphate buffer was 10 mM. The results of the evaluation of the stability of GH Formulation 3 and GH Formulation 4 are shown in Table 9 and Table 10, respectively. In the long-term storage test, the pH, the monomer (%), and the quantity (%) were measured at the start time of the storage, 1 month after, 2 months after, 3 months after, 6 months after, and 9 months after the start time of the storage. In both formulations, in the storage period of the long-term storage test, the pH, the monomer (%), and the quantity (%) were hardly changed, and had values substantially identical to those of GH Formulation 1. In the accelerated test, the pH, the monomer (%), and the quantity (%) were measured 1 month after, 2 months after, and 3 months after the start of the storage. In both formulations, in the storage period of the accelerated test, the pH, the monomer (%), and the quantity (%) were hardly changed, and had values substantially identical to those of GH Formulation 1. Such results indicate that GH Formulations 3 and 4 have stability equivalent to that of GH Formulation 1, and GH Formulations 3 and 4 are expected to be stable in a dark place at a temperature of 2 to 8° C. for at least 24 months. In addition, in a case where standard values of the monomer amount (%) and the quantity (%) are set to be greater than or equal to 98% and greater than or equal to 100%, respectively, GH Formulations 3 and 4 are expected to satisfy the standard value even 36 months after the start time of the storage, when being stored in a dark place at a temperature of 2 to 8° C.

TABLE 9

Table 9 Stability of aqueous preparation (GF Formulation 3)

| Categories | Time point Starting point | pH 6.1 | Monomer (%) 99.5 | Quantity (%) 106 |
|---|---|---|---|---|
| Long term Storage Test (2~8° C.) | 1 month | 6.1 | 99.5 | 105 |
|  | 2 months | 6.2 | 99.5 | 107 |
|  | 3 months | 6.1 | 99.5 | 107 |
|  | 6months | 6.2 | 99.5 | 106 |
|  | 9 months | 6.2 | 99.5 | 105 |
| Accelerated Test (25° C.) | 1 month | 6.2 | 99.4 | 105 |
|  | 2 months | 6.2 | 99.2 | 106 |
|  | 3 months | 6.2 | 99.1 | 107 |

TABLE 10

Table 10 Stability of aqueous preparation (GH Formulation 4)

| Categories | Time point | pH | Monomer (%) | Quantity (%) |
|---|---|---|---|---|
| | Starting point | 6.3 | 99.5 | 105 |
| Long-term Storage Test (2~8° C.) | 1 month | 6.3 | 99.5 | 105 |
| | 2 months | 6.3 | 99.5 | 107 |
| | 3 months | 6.3 | 99.5 | 108 |
| | 6 months | 6.3 | 99.5 | 105 |
| | 9 months | 6.3 | 99.4 | 105 |
| Accelerated Test (25° C.) | 1 months | 6.3 | 99.3 | 105 |
| | 2 month | 6.3 | 99.0 | 106 |
| | 3 months | 6.3 | 98.9 | 107 |

[Example 6] Measurement of Monomer (%) of Growth Hormone and Quantification of Growth Hormone The measurement of the monomer (%) was performed by analyzing a sample with size-exclusion HPLC (SE-HPLC). TSKgel G3000SWXL (an inner diameter of 7.8 mm×30 cm, manufactured by Tosoh Corporation) filled with hydrophilic silica gel for liquid chromatography, having exclusion limit molecular weight of $5 \times 10^5$ and a particle diameter of 5 μm, was set in a fast-performance liquid chromatography device LC-20A (including System Controller CBM-20A, Online Deaeration Unit DGU-20A5R, Liquid Feeding Unit LC-20AB, Autosampler SIL-20AC, Column Oven CTO-20AC, and Ultraviolet-Visible Detector SPD-20AV or SPD-20A, SHIMADZU CORPORATION). The column was equilibrated in a mobile phase (that was prepared by dissolving 15.6 g of sodium dihydrogen phosphate hydrate, 35.8 g of disodium hydrogen phosphate dodecahydrate, and 11.7 g of sodium chloride in water to be 1000 mL, and filtering by using a membrane filter having a pore diameter of 0.22 μm), the sample diluted with pure water such that the concentration of the growth hormone was 1 to 2 mg/mL was applied thereto, an absorbance of 215 nm was monitored, and thus, the elution profile was prepared. The flow rate was 0.5 mL/minute. The monomer (%) was calculated from the area of a peak corresponding to the monomer on the elution profile (monomer peak area) and the area of a peak corresponding to the dimer (dimer peak area), by a calculation formula: Monomer (%)=monomer peak area/(monomer peak area+dimer peak area)×100(%).

A standard curve was prepared by analyzing a growth hormone having a known concentration with SE-HPLC, and the monomer peak area was interpolated thereto, and thus, the growth hormone existing as the monomer in the sample was quantified. Theoretical value of the growth hormone contained in the solution at the start time of the storage, which was calculated from the standard curve, was set to 100%, and the quantitative values of each sample was calculated as the quantity (%).

INDUSTRIAL APPLICABILITY

According to the present invention, an aqueous preparation containing a protein as an active ingredient which is stable in storage in solution and makes an injection pain reduced can be provided.

The invention claimed is:

1. An aqueous preparation, comprising
8 to 12 mM of a phosphate buffer; 4 to 8 mg/mL of growth hormone; 2 mg/mL of poloxamer 188; 3.3 mg/mL of phenol; and D-mannitol,
wherein the aqueous preparation has a pH of 6.2, an osmotic pressure ratio of 0.9 to 1.1, and does not include NaCl.

2. An aqueous preparation, consisting of 10 mM of a phosphate buffer; 4 or 8 mg/mL of growth hormone; 2 mg/mL of poloxamer 188; 3.3 mg/mL of phenol; and 40 mg/mL of D-mannitol,
wherein the aqueous preparation has a pH of 6.2 and an osmotic pressure ratio of 0.9 to 1.1.

3. The aqueous preparation of claim 2, wherein the aqueous preparation includes 4 mg/mL of growth hormone.

4. The aqueous preparation of claim 2, wherein the aqueous preparation includes 8 mg/mL of growth hormone.

* * * * *

UNITED STATES PATENT AND TRADEMARK OFFICE
CERTIFICATE OF CORRECTION

| | | |
|---|---|---|
| PATENT NO. | : 11,738,068 B2 | Page 1 of 1 |
| APPLICATION NO. | : 17/253458 | |
| DATED | : August 29, 2023 | |
| INVENTOR(S) | : Yasukawa et al. | |

It is certified that error appears in the above-identified patent and that said Letters Patent is hereby corrected as shown below:

On the Title Page

Column 2, Item (56), under "OTHER PUBLICATIONS", Line 6, delete "transration," and insert -- translation, --, therefor.

Column 2, Item (57), under "ABSTRACT", Line 10, delete "a" and insert -- an --, therefor.

In the Specification

In Column 3, Line 4, delete "DNaseT," and insert -- DNaseI, --, therefor.

In Column 5, Line 8, delete "S galactosidase," and insert -- β-galactosidase, --, therefor.

In Column 5, Line 43, delete "$" and insert -- β- --, therefor.

In Column 19, Line 11, delete "months" and insert -- month --, therefor.

In Column 19, Line 12, delete "month" and insert -- months --, therefor.

Signed and Sealed this
Sixteenth Day of July, 2024

Katherine Kelly Vidal
*Director of the United States Patent and Trademark Office*